US009526567B2

(12) United States Patent (10) Patent No.: US 9,526,567 B2
Chernov et al. (45) Date of Patent: Dec. 27, 2016

(54) THREAD-LIKE KNIFE FOR TISSUE CUTTING

(71) Applicants: COVIDIEN LP, Mansfield, MA (US); Nataliya Chernova, Saint-Petersburg (RU)

(72) Inventors: Boris Chernov, Saint-Petersburg (RU); Igoris Misuchenko, Saint-Petersburg (RU); Georgy Martsinovskiy, Saint-Petersburg (RU); Mikhail Verbitsky, Stoughton, MA (US)

(73) Assignee: COVIDIEN LP, Mansfield, MA (US)

( * ) Notice: Subject to any disclaimer, the term of this patent is extended or adjusted under 35 U.S.C. 154(b) by 494 days.

(21) Appl. No.: 14/183,217

(22) Filed: Feb. 18, 2014

(65) Prior Publication Data

US 2014/0163553 A1 Jun. 12, 2014

Related U.S. Application Data

(62) Division of application No. 13/108,441, filed on May 16, 2011, now Pat. No. 8,685,009.

(51) Int. Cl.
*A61B 18/14* (2006.01)
*A61B 17/32* (2006.01)
(Continued)

(52) U.S. Cl.
CPC ......... *A61B 18/1447* (2013.01); *A61B 17/295* (2013.01); *A61B 17/320092* (2013.01);
(Continued)

(58) Field of Classification Search
CPC . A81B 18/1447; A81B 18/082; A81B 18/085; A81B 18/1442; A61B 17/295; A61B 17/320068; A61B 17/320092; A61B 2018/1452; A61B 2017/32006
See application file for complete search history.

(56) References Cited

U.S. PATENT DOCUMENTS 2,031,682 A * 2/1936 Wappler ............. A61B 18/1442
606/46
2,068,721 A 1/1937 Wappler
(Continued)

FOREIGN PATENT DOCUMENTS

CN 201299462 9/2009
DE 2415263 A1 10/1975
(Continued)

OTHER PUBLICATIONS

Int'l Search Report PCT/US98/24281 dated Feb. 22, 1999.
(Continued)

*Primary Examiner* — Gary Jackson
*Assistant Examiner* — Boniface N Nganga

(57) ABSTRACT

An end effector assembly for use with an electrosurgical instrument is provided. The end effector assembly includes a pair of opposing jaw members configured to grasp tissue therebetween. The assembly also includes a thread-like member having a first end coupled to at least one jaw member and a drive member coupled to a second end of the thread-like member. The drive member is configured to position the thread-like member between a first position and a second position, wherein the thread-like member cuts tissue when positioned in the second position.

13 Claims, 7 Drawing Sheets

(51) Int. Cl.
*A61B 17/295* (2006.01)
*A61B 18/08* (2006.01)

(52) U.S. Cl.
CPC .. *A61B 18/1442* (2013.01); *A61B 17/320068* (2013.01); *A61B 18/082* (2013.01); *A61B 18/085* (2013.01); *A61B 18/1445* (2013.01); *A61B 2017/32006* (2013.01); *A61B 2018/1452* (2013.01)

(56) References Cited

U.S. PATENT DOCUMENTS

| | | | |
|---|---|---|---|
| 3,495,590 A | | 2/1970 | Zeiller |
| D249,549 S | | 9/1978 | Pike |
| D263,020 S | | 2/1982 | Rau, III |
| D295,893 S | | 5/1988 | Sharkany et al. |
| D295,894 S | | 5/1988 | Sharkany et al. |
| D298,353 S | | 11/1988 | Manno |
| D299,413 S | | 1/1989 | DeCarolis |
| D343,453 S | | 1/1994 | Noda |
| D348,930 S | | 7/1994 | Olson |
| D349,341 S | | 8/1994 | Lichtman et al. |
| D354,564 S | | 1/1995 | Medema |
| D358,887 S | | 5/1995 | Feinberg |
| D384,413 S | | 9/1997 | Zlock et al. |
| H1745 H | | 8/1998 | Paraschac |
| D402,028 S | | 12/1998 | Grimm et al. |
| D408,018 S | | 4/1999 | McNaughton |
| D416,089 S | | 11/1999 | Barton et al. |
| D424,694 S | | 5/2000 | Tetzlaff et al. |
| D425,201 S | | 5/2000 | Tetzlaff et al. |
| H1904 H | | 10/2000 | Yates et al. |
| D449,886 S | | 10/2001 | Tetzlaff et al. |
| D453,923 S | | 2/2002 | Olson |
| D454,951 S | | 3/2002 | Bon |
| D457,958 S | | 5/2002 | Dycus et al. |
| D457,959 S | | 5/2002 | Tetzlaff et al. |
| H2037 H | | 7/2002 | Yates et al. |
| D465,281 S | | 11/2002 | Lang |
| D466,209 S | | 11/2002 | Bon |
| D493,888 S | | 8/2004 | Reschke |
| D496,997 S | | 10/2004 | Dycus et al. |
| D499,181 S | | 11/2004 | Dycus et al. |
| D502,994 S | | 3/2005 | Blake, III |
| D509,297 S | | 9/2005 | Wells |
| D525,361 S | | 7/2006 | Hushka |
| 7,083,618 B2 | | 8/2006 | Couture et al. |
| 7,101,371 B2 | | 9/2006 | Dycus et al. |
| 7,101,372 B2 | | 9/2006 | Dycus et al. |
| D531,311 S | | 10/2006 | Guerra et al. |
| D533,274 S | | 12/2006 | Visconti et al. |
| D533,942 S | | 12/2006 | Kerr et al. |
| D535,027 S | | 1/2007 | James et al. |
| D538,932 S | | 3/2007 | Malik |
| D541,418 S | | 4/2007 | Schechter et al. |
| D541,611 S | | 5/2007 | Aglassinger |
| D541,938 S | | 5/2007 | Kerr et al |
| D545,432 S | | 6/2007 | Watanabe |
| D547,154 S | | 7/2007 | Lee |
| 7,267,677 B2 | | 9/2007 | Johnson et al. |
| D564,662 S | | 3/2008 | Moses et al. |
| D567,943 S | | 4/2008 | Moses et al. |
| D575,395 S | | 8/2008 | Hushka |
| D575,401 S | | 8/2008 | Hixson et al. |
| D582,038 S | | 12/2008 | Swoyer et al. |
| 7,582,087 B2 | | 9/2009 | Tetzlaff et al. |
| 7,594,916 B2 | | 9/2009 | Weinberg |
| D617,900 S | | 6/2010 | Kingsley et al. |
| D617,901 S | | 6/2010 | Unger et al. |
| D617,902 S | | 6/2010 | Twomey et al. |
| D617,903 S | | 6/2010 | Unger et al. |
| D618,798 S | | 6/2010 | Olson et al. |
| D621,503 S | | 8/2010 | Otten et al. |
| D627,462 S | | 11/2010 | Kingsley |
| D628,289 S | | 11/2010 | Romero |
| D628,290 S | | 11/2010 | Romero |
| D630,324 S | | 1/2011 | Reschke |
| 7,922,718 B2 | | 4/2011 | Moses et al. |
| D649,249 S | | 11/2011 | Guerra |
| D649,643 S | | 11/2011 | Allen, IV et al. |
| 8,147,489 B2 | | 4/2012 | Moses |
| D661,394 S | | 6/2012 | Romero et al. |
| 8,298,233 B2 | | 10/2012 | Mueller |
| 8,394,096 B2 | | 3/2013 | Moses |
| 8,409,246 B2 | | 4/2013 | Kerr |
| 8,409,247 B2 | | 4/2013 | Garrison |
| 8,425,511 B2 | | 4/2013 | Olson |
| 8,430,877 B2 | | 4/2013 | Kerr |
| 8,439,913 B2 | | 5/2013 | Horner |
| 8,469,716 B2 | | 6/2013 | Fedotov |
| 8,469,991 B2 | | 6/2013 | Kerr |
| 8,469,992 B2 | | 6/2013 | Roy |
| 8,480,671 B2 | | 7/2013 | Mueller |
| 8,491,624 B2 | | 7/2013 | Kerr |
| 8,491,625 B2 | | 7/2013 | Horner |
| 8,491,626 B2 | | 7/2013 | Roy |
| 8,512,336 B2 | | 8/2013 | Couture |
| 8,540,749 B2 | | 9/2013 | Garrison |
| 8,551,091 B2 | | 10/2013 | Couture |
| 8,556,929 B2 | | 10/2013 | Harper |
| 8,568,397 B2 | | 10/2013 | Horner |
| 8,568,408 B2 | | 10/2013 | Townsend |
| 8,585,736 B2 | | 11/2013 | Horner |
| 8,597,295 B2 | | 12/2013 | Kerr |
| 8,623,018 B2 | | 1/2014 | Horner |
| 8,628,557 B2 | | 1/2014 | Collings |
| 8,637,069 B2 | | 1/2014 | Claude et al. |
| 8,641,712 B2 | | 2/2014 | Couture |
| 8,647,343 B2 | | 2/2014 | Chojin |
| 8,652,135 B2 | | 2/2014 | Nau, Jr. |
| 8,663,222 B2 | | 3/2014 | Anderson |
| 8,672,939 B2 | | 3/2014 | Garrison |
| 8,685,009 B2 | | 4/2014 | Chernov |
| 8,685,021 B2 | | 4/2014 | Chernov |
| 8,702,749 B2 | | 4/2014 | Twomey |
| 8,734,445 B2 | | 5/2014 | Johnson |
| 8,740,898 B2 | | 6/2014 | Chojin |
| 8,745,840 B2 | | 6/2014 | Hempstead |
| 2006/0217706 A1* | | 9/2006 | Lau .................. A61B 18/1445 606/45 |
| 2006/0229600 A1* | | 10/2006 | Canady ............ A61B 18/042 606/45 |
| 2007/0118111 A1* | | 5/2007 | Weinberg ......... A61B 18/1445 606/45 |
| 2008/0163432 A1 | | 7/2008 | Twomey |
| 2011/0054467 A1* | | 3/2011 | Mueller ............. A61B 17/295 606/45 |
| 2011/0190765 A1 | | 8/2011 | Chojin |
| 2011/0193608 A1 | | 8/2011 | Krapohl |
| 2011/0218530 A1 | | 9/2011 | Reschke |
| 2011/0251605 A1 | | 10/2011 | Hoarau |
| 2011/0270245 A1 | | 11/2011 | Horner |
| 2011/0270251 A1 | | 11/2011 | Horner |
| 2011/0276048 A1 | | 11/2011 | Kerr |
| 2011/0276049 A1 | | 11/2011 | Gerhardt |
| 2011/0295313 A1 | | 12/2011 | Kerr |
| 2011/0319888 A1 | | 12/2011 | Mueller |
| 2012/0022532 A1 | | 1/2012 | Garrison |
| 2012/0041438 A1 | | 2/2012 | Nau, Jr. |
| 2012/0046662 A1 | | 2/2012 | Gilbert |
| 2012/0059372 A1 | | 3/2012 | Johnson |
| 2012/0059375 A1 | | 3/2012 | Couture |
| 2012/0059408 A1 | | 3/2012 | Mueller |
| 2012/0059409 A1 | | 3/2012 | Reschke |
| 2012/0083785 A1 | | 4/2012 | Roy |
| 2012/0083786 A1 | | 4/2012 | Artale |
| 2012/0083827 A1 | | 4/2012 | Artale |
| 2012/0095460 A1 | | 4/2012 | Rooks |
| 2012/0109187 A1 | | 5/2012 | Gerhardt, Jr. |
| 2012/0123402 A1 | | 5/2012 | Chernov |
| 2012/0123404 A1 | | 5/2012 | Craig |
| 2012/0123410 A1 | | 5/2012 | Craig |
| 2012/0130367 A1 | | 5/2012 | Garrison |
| 2012/0136353 A1 | | 5/2012 | Romero |

(56) References Cited

U.S. PATENT DOCUMENTS

| | | |
|---|---|---|
| 2012/0136354 A1 | 5/2012 | Rupp |
| 2012/0172868 A1 | 7/2012 | Twomey |
| 2012/0172924 A1 | 7/2012 | Allen, IV |
| 2012/0215219 A1 | 8/2012 | Roy |
| 2012/0239034 A1 | 9/2012 | Horner |
| 2012/0253344 A1 | 10/2012 | Dumbauld |
| 2012/0259331 A1 | 10/2012 | Garrison |
| 2012/0265241 A1 | 10/2012 | Hart |
| 2012/0283727 A1 | 11/2012 | Twomey |
| 2012/0283734 A1 | 11/2012 | Ourada |
| 2012/0296205 A1 | 11/2012 | Chernov |
| 2012/0296238 A1 | 11/2012 | Chernov |
| 2012/0296239 A1 | 11/2012 | Chernov |
| 2012/0296317 A1 | 11/2012 | Chernov |
| 2012/0296323 A1 | 11/2012 | Chernov |
| 2012/0296324 A1 | 11/2012 | Chernov |
| 2012/0296332 A1 | 11/2012 | Chernov |
| 2012/0296333 A1 | 11/2012 | Twomey |
| 2012/0296334 A1 | 11/2012 | Kharin |
| 2012/0303025 A1 | 11/2012 | Garrison |
| 2012/0323238 A1 | 12/2012 | Tyrrell |
| 2012/0330308 A1 | 12/2012 | Joseph |
| 2012/0330309 A1 | 12/2012 | Joseph |
| 2013/0018364 A1 | 1/2013 | Chernov |
| 2013/0018371 A1 | 1/2013 | Twomey |
| 2013/0018372 A1 | 1/2013 | Sims |
| 2013/0022495 A1 | 1/2013 | Allen, IV |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 10031773 | 11/2001 |
| DE | 19946527 | 12/2001 |
| DE | 20121161 | 4/2002 |
| DE | 10045375 C2 | 10/2002 |
| DE | 20 2007 009318 | 8/2007 |
| DE | 202007009165 U1 | 8/2007 |
| DE | 202007009317 U1 | 8/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1 159 926 A2 | 12/2001 |
| EP | 1281878 | 10/2005 |
| JP | 61-501068 | 9/1984 |
| JP | 10-24051 A | 1/1989 |
| JP | 11-47150 A | 6/1989 |
| JP | WO 9012884 A1 * | 11/1990 ............ C07K 16/24 |
| JP | 6-502328 | 3/1992 |
| JP | 5-5106 | 1/1993 |
| JP | 05-40112 | 2/1993 |
| JP | 6-030945 | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-317936 | 3/1996 |
| JP | 8-56955 | 5/1996 |
| JP | 8-289895 | 5/1996 |
| JP | 08252263 A | 10/1996 |
| JP | 8-317934 A | 12/1996 |
| JP | 9-10223 C | 1/1997 |
| JP | 9-122138 A | 5/1997 |
| JP | 10-000195 | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 | 5/2000 |
| JP | 2000342599 A | 12/2000 |
| JP | 2000350732 A | 12/2000 |
| JP | 2001-8944 | 1/2001 |
| JP | 2001-29356 | 2/2001 |
| JP | 2001-128990 | 5/2001 |
| JP | 2001128990 A | 5/2001 |
| JP | 2001-190564 A | 7/2001 |
| JP | 2001-3400 | 11/2001 |
| JP | 2002-528166 | 3/2002 |
| JP | 2002-136525 | 5/2002 |
| JP | 2002230073 A * | 8/2002 |
| JP | 2003-116871 | 4/2003 |
| JP | 2003-175052 | 6/2003 |
| JP | 2003-245285 | 9/2003 |
| JP | 2004-517668 A | 6/2004 |
| JP | 2004-528869 A | 9/2004 |
| JP | 2005-152663 | 6/2005 |
| JP | 2005-253789 | 9/2005 |
| JP | 2005-312807 | 10/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | 0036986 A1 | 6/2000 |
| WO | WO 00/59392 | 10/2000 |
| WO | 0115614 A1 | 3/2001 |
| WO | 0154604 A1 | 8/2001 |
| WO | WO 02/45589 | 6/2002 |
| WO | 2005/110264 A2 | 11/2005 |
| WO | WO 2006/021269 | 3/2006 |
| WO | WO 2008/040483 | 4/2008 |
| WO | WO 2011/018154 | 2/2011 |

OTHER PUBLICATIONS

Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.

(56) References Cited

OTHER PUBLICATIONS

Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 185386.9 dated Jan. 10, 2011.
Int'l Search Report EP 10 185405.7 dated Jan. 5, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182022.3 dated Mar. 11, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 161117.4 dated Jun. 30, 2011.
Int'l Search Report PCT/US98/18640 dated Jan. 29, 1999.
Int'l Search Report PCT/US98/23950 dated Jan. 14, 1999.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967, British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.

(56) References Cited

OTHER PUBLICATIONS

LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.

* cited by examiner

THREAD-LIKE KNIFE FOR TISSUE CUTTING

CROSS-REFERENCE TO RELATED APPLICATION

The present application is a divisional application of U.S. patent application Ser. No. 13/108,441, filed on May 16, 2011, the entire content of which is hereby incorporated by reference herein.

BACKGROUND

1. Technical Field

The present disclosure relates to electrosurgical instruments used for open and endoscopic surgical procedures for sealing or fusing tissue. More particularly, the present disclosure relates to a bipolar forceps used in an energy based sealing instrument and configured to cut tissue, and, in particular, cut tissue using a thread-like knife.

2. Background of the Related Art

Open or endoscopic electrosurgical forceps utilize both mechanical clamping action and electrical energy to effect hemostasis. The electrode of each opposing jaw member is charged to a different electric potential such that when the jaw members grasp tissue, electrical energy can be selectively transferred through the tissue. A surgeon can cauterize, coagulate/desiccate and/or simply reduce or slow bleeding, by controlling the intensity, frequency and duration of the electrosurgical energy applied between the electrodes and through the tissue.

Certain surgical procedures require more than simply cauterizing tissue and rely on the combination of clamping pressure, electrosurgical energy and gap distance to "seal" tissue, vessels and certain vascular bundles. More particularly, vessel sealing or tissue sealing utilizes a unique combination of radiofrequency (RF) energy, clamping pressure and precise control of gap distance (i.e., distance between opposing jaw members when closed about tissue) to effectively seal or fuse tissue between two opposing jaw members or sealing plates. Vessel or tissue sealing is more than "cauterization", which involves the use of heat to destroy tissue (also called "diathermy" or "electrodiathermy"). Vessel sealing is also more than "coagulation", which is the process of desiccating tissue wherein the tissue cells are ruptured and dried. "Vessel sealing" is defined as the process of liquefying the collagen, elastin and ground substances in the tissue so that the tissue reforms into a fused mass with significantly-reduced demarcation between the opposing tissue structures.

Many electrosurgical instruments include a cutting member for cutting sealed tissue. Existing methods involve the use mechanical or electrical cutting actions. For example, a knife may be included in an electrosurgical instrument. The knife is designed to cut a thin layer of tissue grasped between jaws. Conventional instruments do not allow use of the knife unless the jaws are closed. However, sometimes there is a need for cutting and sealing thicker tissues where the jaws cannot completely close and the thicker tissue has to be cut without sealing.

SUMMARY

In an embodiment of the present disclosure, an end effector assembly is provided. The end effector assembly includes a pair of opposing jaw members configured to grasp tissue therebetween. The assembly also includes a thread-like member having a first end coupled to at least one jaw member and a drive member coupled to a second end of the thread-like member. The drive member is configured to position the thread-like member between a first position and a second position, wherein the thread-like member cuts tissue when positioned in the second position.

The drive member may include a drive shaft having a spring component and at least one guiding roll configured to hold the second end of the thread like member and guide the thread-like member between the first position and the second position.

The thread-like member may be a bow shaped spring that is coupled to at least one jaw member with a hinge. A cutting portion of the thread-like member may be formed from twisted filaments, include a resistive conductor or include a fiber waveguide such as an optical fiber. The optical fiber may include a side-lit fiber or a long period fiber grating.

In yet another embodiment of the present disclosure another electrosurgical instrument for sealing tissue is provided. The end effector assembly includes a pair of opposing jaw members configured to grasp tissue therebetween. The assembly also includes a thread-like member formed as a continuous loop and a drive member. The drive member is configured to position the thread-like member between a first position and a second position, wherein the thread-like member cuts tissue when positioned in the second position. A drive drum may also be provided that is operatively coupled to the thread-like member and configured to move the thread-like member to cut tissue between the pair of opposing jaw members.

In another embodiment of the present disclosure, a method for cutting tissue using an end effector assembly including a pair of opposing jaw members and a thread-like member is provided. The method includes sealing tissue between the pair of opposing jaw members, and activating a drive member to move the thread-like member distally and cut the sealed tissue.

BRIEF DESCRIPTION OF THE DRAWINGS

Objects and features of the presently disclosed systems and methods will become apparent to those of ordinary skill in the art when descriptions of various embodiments thereof are read with reference to the accompanying drawings, of which.

DETAILED DESCRIPTION

Figure 1:
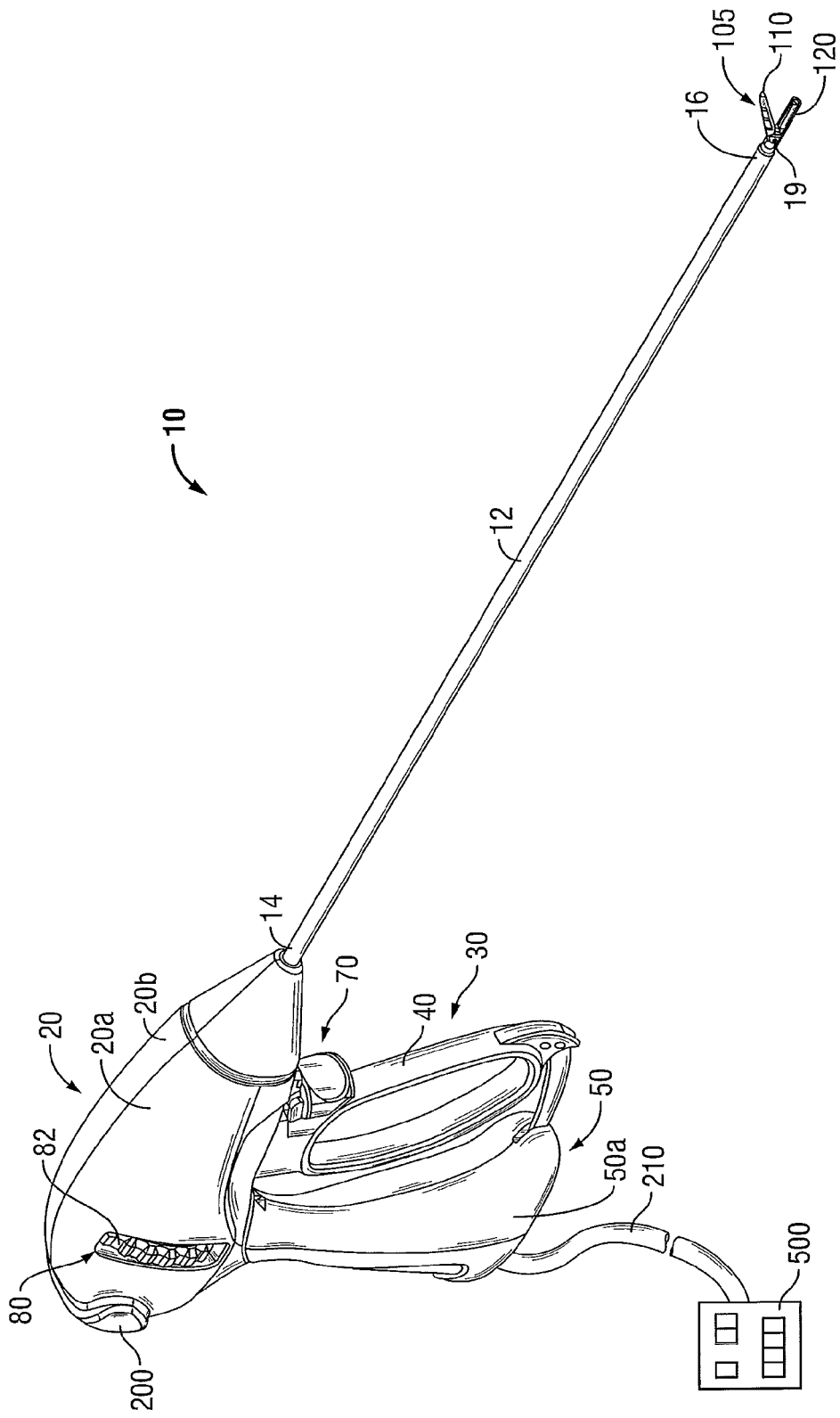
FIG. 1 is a right, perspective view of an endoscopic bipolar forceps having a housing, a shaft and a pair of jaw members affixed to a distal end thereof, the jaw members including an electrode assembly disposed therebetween.

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

Electromagnetic energy is generally classified by increasing frequency or decreasing wavelength into radio waves, microwaves, infrared, visible light, ultraviolet, X-rays and gamma-rays. As used herein, the term "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As used herein, the term "RF" generally refers to electromagnetic waves having a lower frequency than microwaves. As used herein, the term "ultrasound" generally refers to cyclic sound pressure with a frequency greater than the upper limit of human hearing. The terms "tissue" and "vessel" may be used interchangeably since it is believed that the present disclosure may be employed to seal and cut tissue or seal and cut vessels utilizing the same principles described herein.

As will be described in more detail below with reference to the accompanying figures, the present disclosure is directed to a thread like knife to cut tissue.

Figure 2:
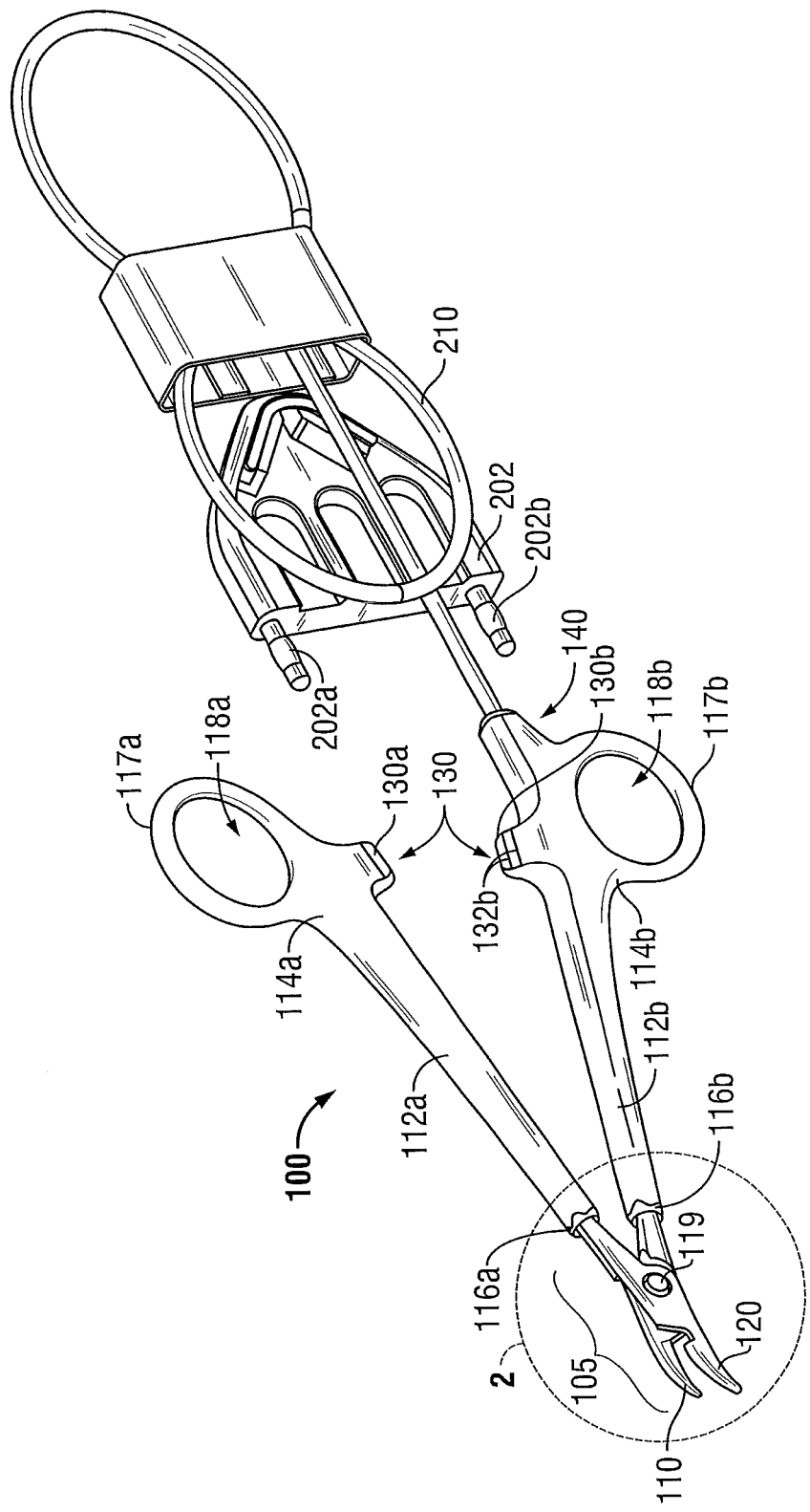
FIG. 2 is a left, perspective view of an open bipolar forceps showing a pair of first and second shafts each having a jaw member affixed to a distal end thereof with an electrode assembly disposed therebetween.

Referring now to FIGS. 1 and 2, FIG. 1 depicts a bipolar forceps 10 for use in connection with endoscopic surgical procedures and FIG. 2 depicts an open forceps 100 contemplated for use in connection with traditional open surgical procedures. For the purposes herein, either an endoscopic instrument or an open instrument may be utilized with the electrode assembly described herein. Different electrical and mechanical connections and considerations may apply to each particular type of instrument; however, the aspects with respect to the electrode assembly and its operating characteristics remain generally consistent with respect to both the open or endoscopic designs.

FIG. 1 shows a bipolar forceps 10 for use with various endoscopic surgical procedures and generally includes a housing 20, a handle assembly 30, a rotating assembly 80, a knife actuator 70 and an electrode assembly 105 having opposing jaw members 110 and 120 that mutually cooperate to grasp, seal and divide tubular vessels and vascular tissue. More particularly, forceps 10 includes a shaft 12 that has a distal end 16 configured to mechanically engage the electrode assembly 105 and a proximal end 14 that mechanically engages the housing 20. The shaft 12 may include one or more suitable mechanically-engaging components that are designed to securely receive and engage the electrode assembly 105 such that the jaw members 110 and 120 are pivotable relative to one another to engage and grasp tissue therebetween.

The proximal end 14 of shaft 12 mechanically engages the rotating assembly 80 to facilitate rotation of the electrode assembly 105. In the drawings and in the descriptions that follow, the term "proximal", as is traditional, will refer to the end of the forceps 10 that is closer to the user, while the term "distal" will refer to the end that is further from the user. Details relating to the mechanically cooperating components of the shaft 12 and the rotating assembly 80 are described in commonly-owned U.S. patent application Ser. No. 10/460,926, now U.S. Pat. No. 7,156,846, entitled "VESSEL SEALER AND DIVIDER FOR USE WITH SMALL TROCARS AND CANNULAS" filed on Jun. 13, 2003.

Handle assembly 30 includes a fixed handle 50 and a movable handle 40. Fixed handle 50 is integrally associated with housing 20 and handle 40 is movable relative to fixed handle 50 to actuate the opposing jaw members 110 and 120 of the electrode assembly 105 as explained in more detail below. Movable handle 40 and knife actuator 70 are of unitary construction and are operatively connected to the housing 20 and the fixed handle 50 during the assembly process. Housing 20 is constructed from two component halves 20a and 20b that are assembled about the proximal end 14 of shaft 12 during assembly. Switch assembly 200 is configured to selectively provide electrical energy to the electrode assembly 105.

As mentioned above, electrode assembly 105 is attached to the distal end 16 of shaft 12 and includes the opposing jaw members 110 and 120. Movable handle 40 of handle assembly 30 imparts movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

Referring now to FIG. 2, an open forceps 100 includes a pair of elongated shaft portions 112a and 112b each having a proximal end 114a and 114b, respectively, and a distal end 116a and 116b, respectively. The forceps 100 includes jaw members 120 and 110 that attach to distal ends 116a and 116b of shafts 112a and 112b, respectively. The jaw members 110 and 120 are connected about pivot pin 119 that allows the jaw members 110 and 120 to pivot relative to one another from the first to second positions for treating tissue. The electrode assembly 105 is connected to opposing jaw members 110 and 120 and may include electrical connections through or around the pivot pin 119. Examples of various electrical connections to the jaw members are shown in commonly-owned U.S. patent application Ser. Nos. 10/474,170, 10/284,562 10/472,295, 10/116,944 and 10/179,863, now U.S. Pat. Nos. 7,582,087, 7,267,677, 7,101,372, 7,083,618 and 7,101,371 respectively.

Each shaft 112a and 112b includes a handle 117a and 117b disposed at the proximal end 114a and 114b thereof that each define a finger hole 118a and 118b, respectively, therethrough for receiving a finger of the user. As can be appreciated, finger holes 118a and 118b facilitate movement of the shafts 112a and 112b relative to one another, which, in turn, pivot the jaw members 110 and 120 from the open position wherein the jaw members 110 and 120 are disposed in spaced relation relative to one another to the clamping or closed position wherein the jaw members 110 and 120 cooperate to grasp tissue therebetween. A ratchet 130 may be included for selectively locking the jaw members 110 and 120 relative to one another at various positions during pivoting.

More particularly, the ratchet 130 includes a first mechanical interface 130a associated with shaft 112a and a second mating mechanical interface 130b associated with shaft 112b. Each position associated with the cooperating ratchet interfaces 130a and 130b holds a specific, i.e., constant, strain energy in the shaft members 112a and 112b, which, in turn, transmits a specific closing force to the jaw members 110 and 120. The ratchet 130 may include graduations or other visual markings that enable the user to easily and quickly ascertain and control the amount of closure force desired between the jaw members 110 and 120.

As best seen in FIG. 2, forceps 100 also includes an electrical interface or plug 202 that connects the forceps 100 to a source of electrosurgical energy, e.g., an electrosurgical generator similar to generator 500 shown in FIG. 1. Plug 202 includes at least two prong members 202*a* and 202*b* that are dimensioned to mechanically and electrically connect the forceps 100 to the electrosurgical generator 500 (See FIG. 1). An electrical cable 210 extends from the plug 202 and securely connects the cable 210 to the forceps 100. Cable 210 is internally divided within the shaft 112*b* to transmit electrosurgical energy through various electrical feed paths to the electrode assembly 105.

One of the shafts, e.g. 112*b*, includes a proximal shaft connector/flange 140 that is designed to connect the forceps 100 to the source of electrosurgical energy such as an electrosurgical generator 500. More particularly, flange 140 mechanically secures electrosurgical cable 210 to the forceps 100 such that the user may selectively apply electrosurgical energy as needed.

Figure 3:
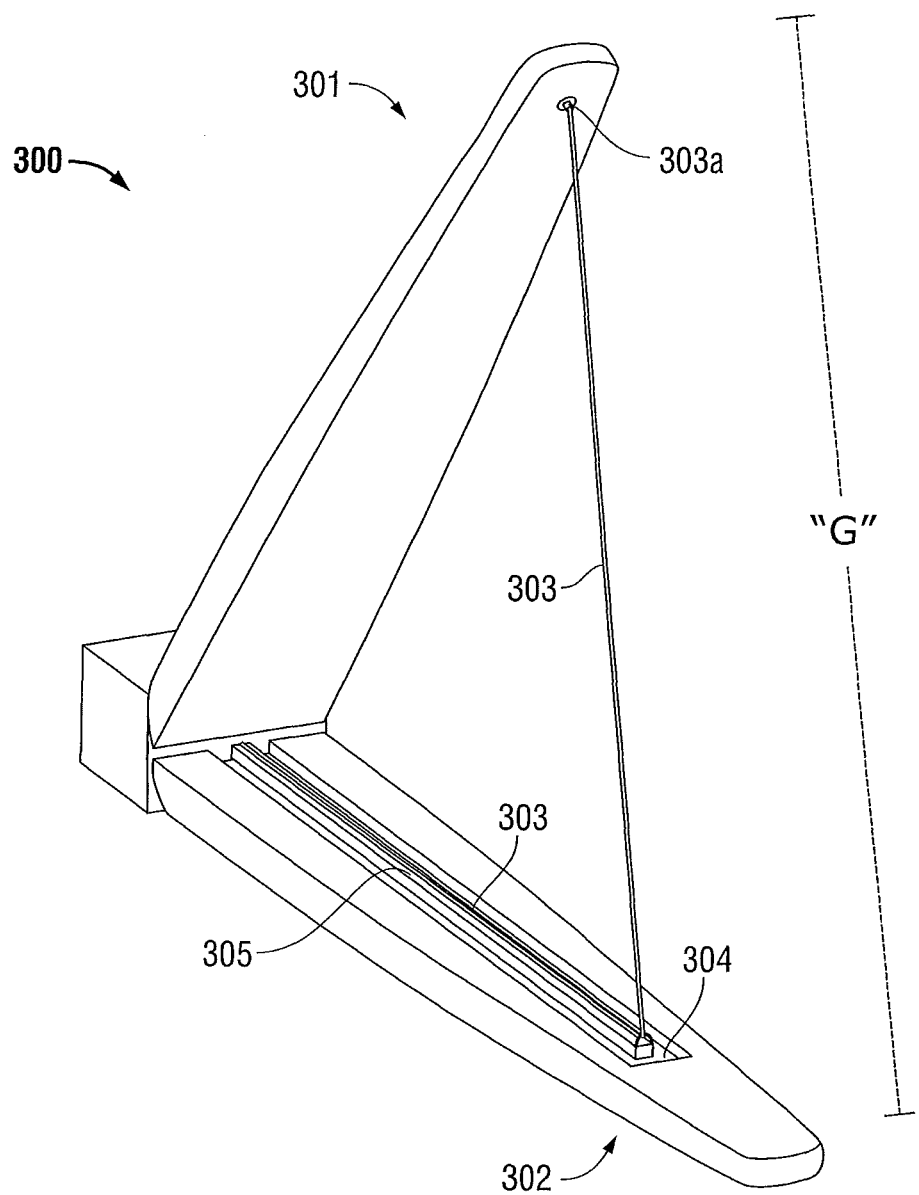
FIG. 3 is a right perspective view of an end effector assembly according to an embodiment of the present disclosure.

FIG. 3 depicts an end effector assembly according to an embodiment of the present disclosure shown generally as end effector 300. End effector assembly 300 includes an upper jaw member 301 and lower jaw member 302. A cutting member or thread-like member 303 spans across the gap between jaw member 301 and jaw member 302. End effector assembly 300 may be used to cut tissue in two modes. In a first mode, thread-like member 303 may be used to cut tissue grasped between jaw members 301 and 302. The tissue may or may not be sealed. In a second mode, thread-like member 303 is stretched between jaw members 301 and 302 to cut tissue that is not grasped by jaw members 301 and 302. This mode may be similar to the use of a surgical scalpel where thread-like member 303 acts a cutting blade. Thread-like member 303 may move between jaw members 301 and 302 to cut the tissue using a saw-like movement.

Thread-like member 303 may be a single filament or composed of multiple filaments bound and tied together or braided. Each filament may be made from a polymer, metal, alloy, optical fiber, composite material, or the like. The portion of thread-like member 303 used to cut tissue may have an irregular surface along the axial direction where the irregularity may be formed by twisted filaments, a barbed structure, abrasive particles attached to thereto, or the like. Thread-like member 303 may also be made from a resistive conductor and coupled to an energy supply that would heat thread-like member 303 to facilitate cutting.

Alternatively, thread-like member 303 may be a fiber waveguide that emits an electromagnetic field to be absorbed by tissue in order to heat the tissue. Thread-like member 303 may be coupled to an energy source (not shown), which may be a stand alone unit or included in generator 500 (FIG. 1) that supplies the electromagnetic energy to thread-like member 303. The fiber waveguide may be an optical fiber waveguide and the energy source may supply optical energy to thread-like member 303. In the portion of thread-like member 303 that directly contacts tissue, waveguiding conditions, such as total internal reflection conditions, may be frustrated and the optical energy leaves thread-like member 303 and penetrates tissue. A rugged side-lit fiber or an optical periodic structure such as long period fiber gratin can be fabricated into thread-like member 303 to increase coupling of energy into the tissue.

As shown in FIG. 3, one end 303*a* of thread-like member 303 is secured to a distal end of jaw member 301. Thread-like member 303 is also coupled to a drive member 305 that is configured to move a cutting portion of thread-like member 303 into gap "G" between jaw members 301 and 302 as will be described hereinbelow with reference to FIGS. 4A-7. Drive member 305 may be actuated by a trigger (not shown). Thread-like member 303 moves along a channel 304 in jaw member 302.

Figure 4A:
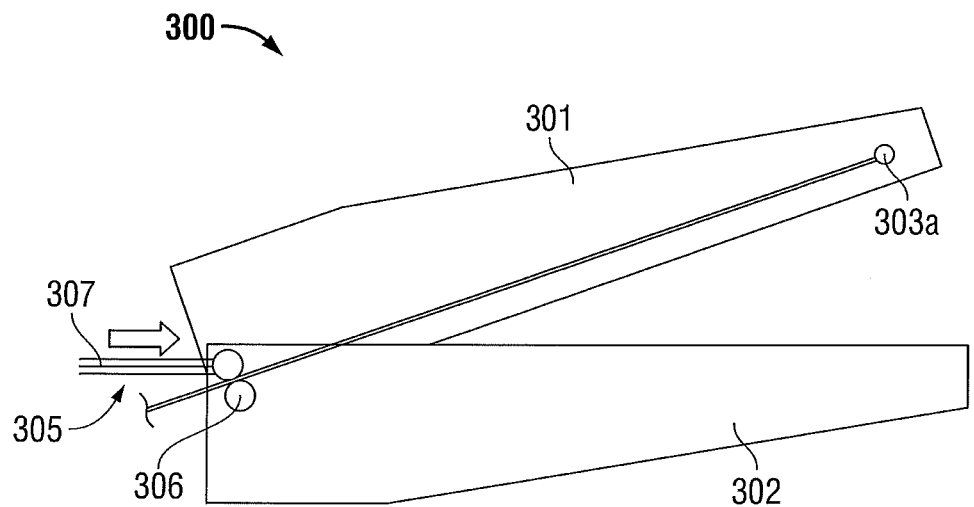
FIGS. 4A and 4B are schematic views of an end effector assembly according to an embodiment of the present disclosure.
Figure 4B:
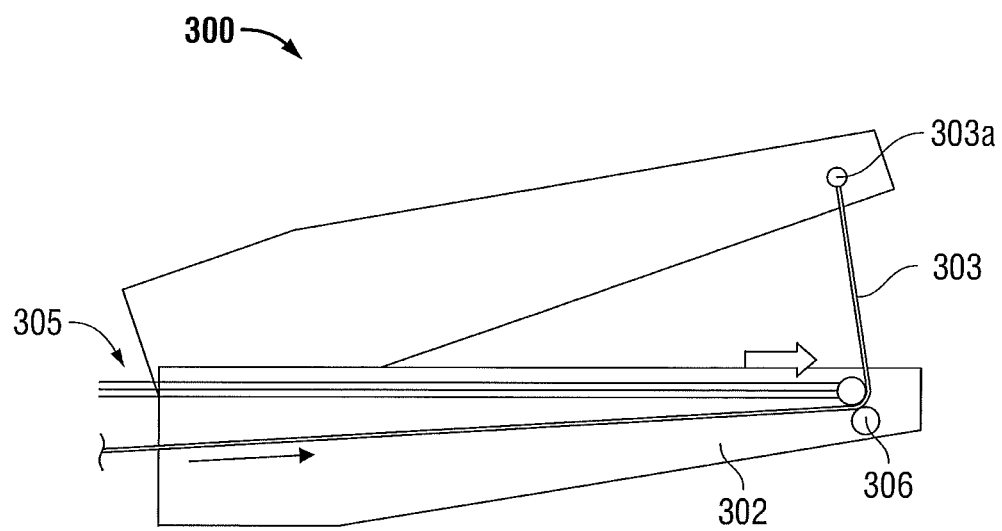

With regard to FIGS. 4A and 4B, FIG. 4A depicts the thread-like member 303 before thread-like member 303 is transitioned into a cutting mode and FIG. 4B, shows thread-like member 303 at the final stage of tissue cutting. As shown in FIGS. 4A and 4B, end effector assembly 300 includes a drive member 305 having a drive shaft 307 and guiding rolls 306 attached to the distal end of drive shaft 307. Drive shaft 307 may include a spring component to provide tension and resilience for thread-like member 303 for any width of gap "G". Drive shaft 307 pushes guiding rolls 306 distally causing thread-like member 303 to move into a cutting mode as shown in FIG. 4B.

As thread-like member 303 is moved into the gap between jaw member 301 and 302, thread-like member 303 cuts tissue disposed between jaw members 301 and 302. As long as end 303*a* of thread-like member 303 is secured to jaw member 301 and the other end of thread-like member 303 is being moved, the portion of thread-like member 303 contacting tissue shifts along thread-like member 303 during movement through the tissue. This reduces the path for which a particular portion of thread-like member 303 contacts tissue thereby reducing contamination of thread-like member 303 by the tissue fragments.

Figure 5A:
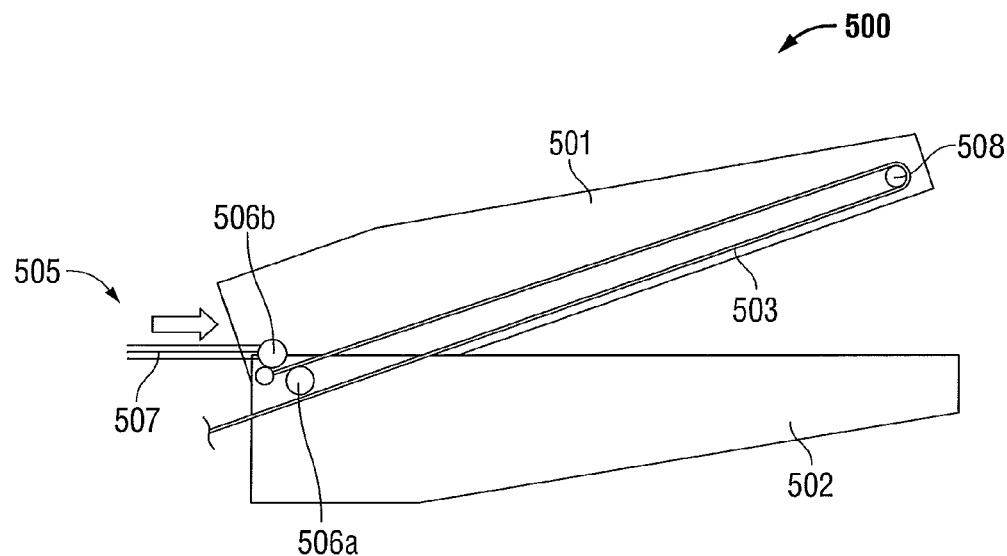
FIGS. 5A and 5B are schematic views of an end effector assembly according to another embodiment of the present disclosure.
Figure 5B:
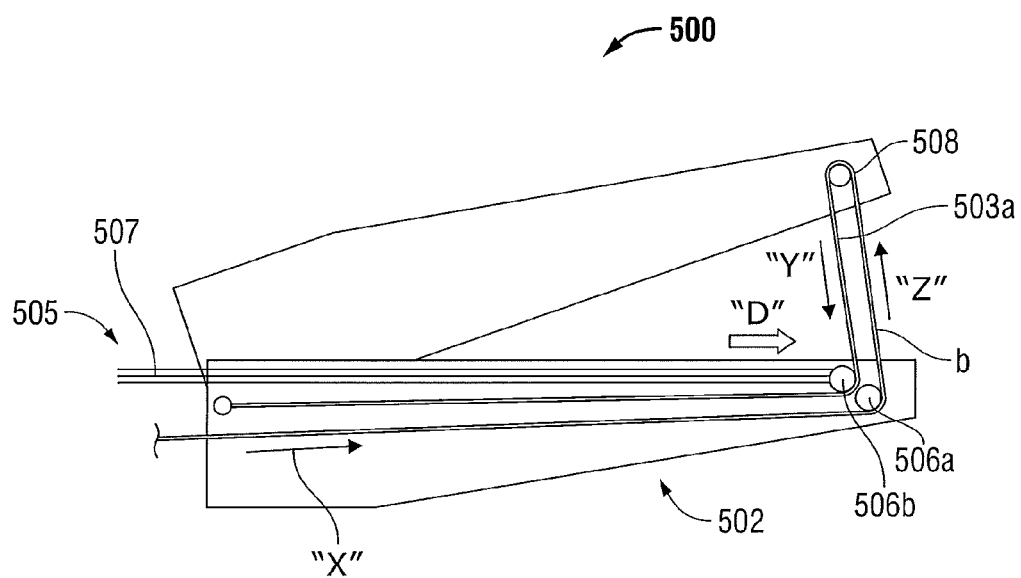

FIGS. 5A and 5B depict an end effector assembly according to another embodiment of the present disclosure shown generally as 500. As shown in FIG. 5A, thread-like member 503 is secured at a proximal portion of end effector assembly 500. Thread-like member 503 is substantially similar to thread-like member 303. Thread-like member 503 extends distally through guiding rolls 506*a* and 506*b* of drive member 505 and is looped around guiding roll 508 at the distal end of jaw member 501. In this arrangement, when shaft 507 of drive member 505 is pushed distally (arrow "D"), two cutting portions 503*a*, 503*b* are moved into the space between jaw members 501 and 502. Additionally, pushing drive member 505 distally also results in movements along the direction of thread-like member stretching as shown by arrows "X", "Y" and "Z". The movement of cutting portions 503*a* and 503*b* along arrows "Y" and "Z" respectively, provide a saw-like operation for thread-like member 303 that eases cutting of tissue.

Figure 6A:
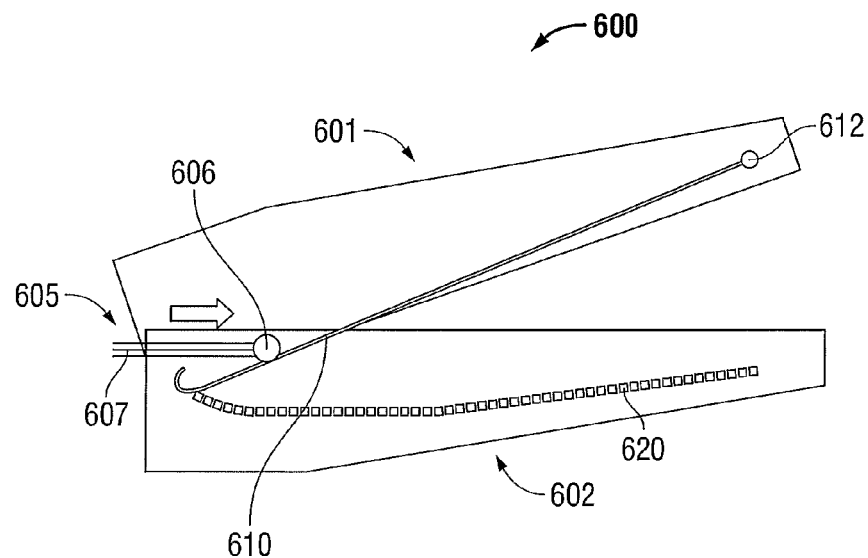
FIGS. 6A and 6B are schematic views of an end effector assembly according to another embodiment of the present disclosure.
Figure 6B:
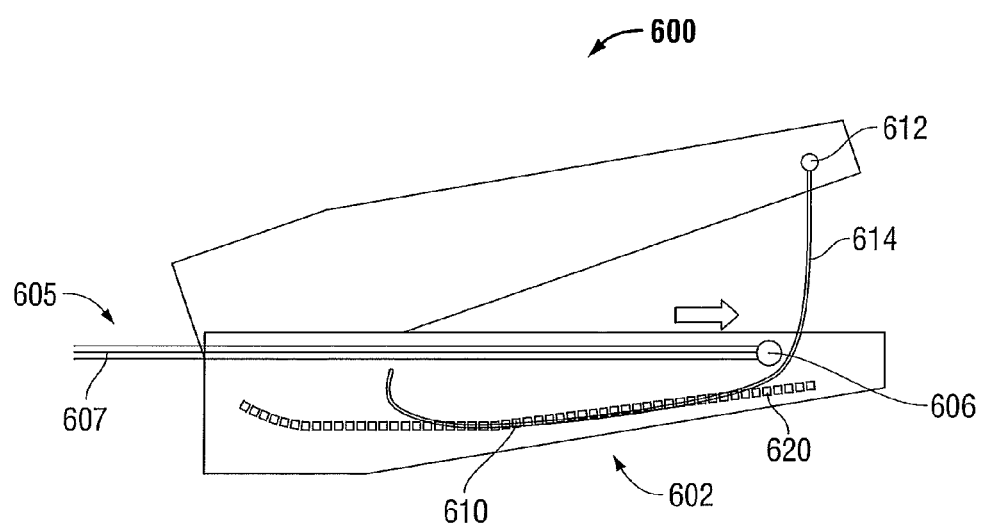

With regard to FIGS. 6A and 6B that show an end effector assembly 600 according to another embodiment of the present disclosure, FIG. 6A depicts a spring 610 before spring 610 is transitioned into a cutting mode, and FIG. 6B shows spring 610 at the final stage of tissue cutting. Spring 610 may be a thin bow-shaped spring made from a shape memory alloy or the like. The distal end of spring 610 may be secured to jaw member 601 with a hinge 612. The proximal end of spring 610 may be moved by drive member 605, which includes drive shaft 607 and guiding roll 606, in a channel 620 in jaw member 602. As drive member 605 is pushed distally, a cutting portion 614 of spring 610 moves into position between the distal end of jaw members 601 and 602 to cut tissue placed therebetween.

Figure 7:
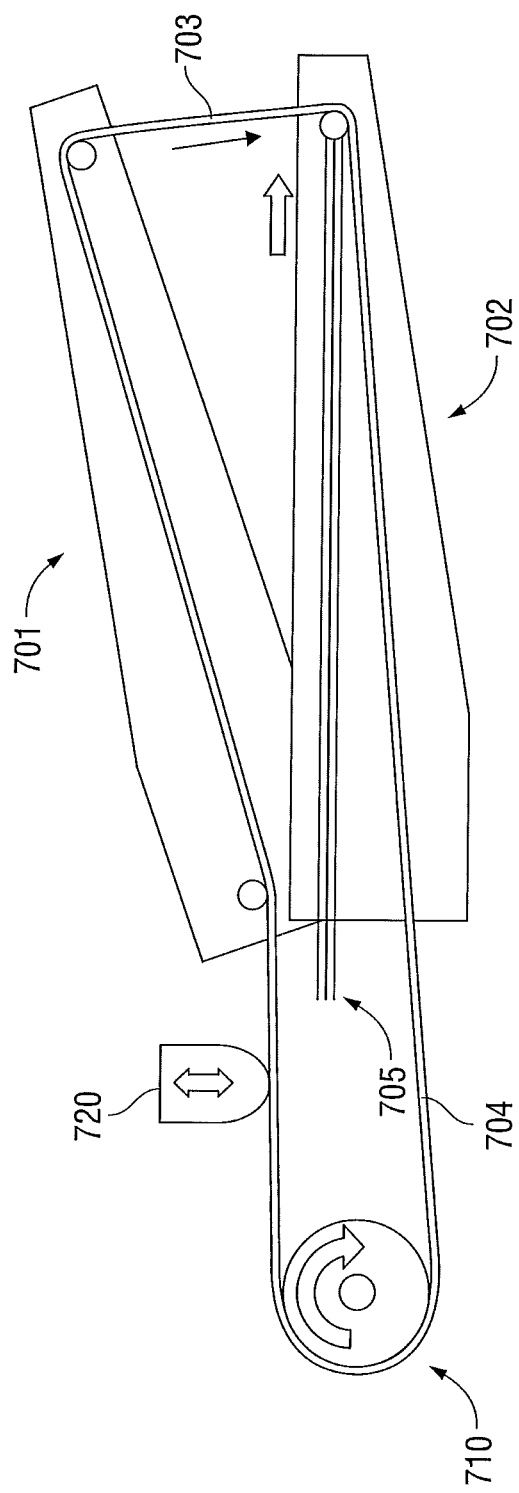
FIG. 7 is a schematic view of an end effector assembly according to an embodiment of the present disclosure.

FIG. 7 depicts an end effector assembly according to another embodiment of the present disclosure. As can be seen in FIG. 7, thread-like member 704 is formed as a continuous loop that is operatively connected to a drive drum 710. When drive member 705 is pushed distally so that cutting portion 703 of thread-like member 704 is positioned between distal end of jaw members 701 and 702, rotation of drive drum 710 causes cutting portion 703 of thread-like member 704 to act as a saw, e.g. a band saw. An ultrasonic transducer 720 may be included to increase the efficiency of cutting portion 703. Ultrasonic transducer 720 may cause cutting portion 703 to excite ultrasonic waves.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. The claims can encompass embodiments in hardware, software, or a combination thereof. Those skilled in the art will envision other modifications within the scope and spirit of the claims appended hereto.

What is claimed is:

1. An end effector assembly, comprising:
   first and second opposing jaw members configured to grasp tissue therebetween;
   a thread-like member formed as a continuous loop;
   a drive member configured to position the thread-like member between a first position and a second position, wherein the thread-like member cuts tissue when transitioned from the first position to the second position; and
   a drive drum operatively coupled to the thread-like member and configured to move the thread-like member to cut tissue between the first and second opposing jaw members.

2. The end effector assembly in accordance with claim 1, wherein the drive member selectively moves between a first position that is further from a distal portion of the second jaw member and a second position that is nearer to a distal portion of the second jaw member.

3. The end effector assembly in accordance with claim 1, wherein the drive drum is configured to rotate when the drive member positions the thread-like member between the first position and the second position.

4. The end effector assembly in accordance with claim 1, wherein the drive drum is configured drive the thread-like member continuously from the first jaw member to the second jaw member in a bandsaw-like manner.

5. The end effector assembly in accordance with claim 1, further comprising a movable guide disposed at a distal end of the drive member.

6. The end effector assembly in accordance with claim 5, wherein the thread-like member is configured to loop around the movable guide.

7. The end effector assembly in accordance with claim 1, further comprising a first stationary guide disposed at a distal end of the first jaw member.

8. The end effector assembly in accordance with claim 7, wherein the thread-like member loops over the first stationary guide.

9. The end effector assembly in accordance with claim 1, further comprising a second stationary guide disposed at a proximal end of the first jaw member.

10. The end effector assembly in accordance with claim 9, wherein the thread-like member loops under the second stationary guide.

11. The end effector assembly in accordance with claim 1, further comprising an ultrasonic transducer disposed in operative communication with the thread-like member.

12. An end effector assembly, comprising:
    first and second opposing jaw members configured to grasp tissue therebetween;
    a drive member disposed within the second jaw member and movable between a first position further from a distal end of the second jaw member and a second position closer to a distal end of the second jaw member;
    a movable guide disposed at a distal end of the drive member;
    a stationary guide disposed at a distal end of the first jaw member;
    a drive drum disposed proximal of the first and second opposing jaw members; and
    a thread-like member forming a continuous loop around the drive drum, the stationary guide, and the movable guide.

13. The end effector in accordance with claim 12, further comprising an ultrasonic transducer disposed in operative communication with the thread-like member.

* * * * *